United States Patent
Huang

(10) Patent No.: US 6,458,598 B1
(45) Date of Patent: Oct. 1, 2002

(54) PROCESS FOR PREPARING AND PRESENTING A TISSUE SAMPLE FOR HISTOLOGICAL STUDY

(75) Inventor: Dennis S. Huang, Carpinteria, CA (US)

(73) Assignee: Dako A/S, Glostrup (DK)

( * ) Notice: Subject to any disclaimer, the term of this patent is extended or adjusted under 35 U.S.C. 154(b) by 0 days.

(21) Appl. No.: 09/929,642

(22) Filed: Aug. 13, 2001

(51) Int. Cl.[7] ............................................. G01N 33/48
(52) U.S. Cl. .................... 436/176; 427/2.11; 427/4; 435/40.5; 435/40.51; 435/40.52
(58) Field of Search ........................ 427/2.11, 2.13, 427/4; 435/40.5, 40.51, 40.52, 30, 374, 378–381, 396, 397; 436/176

(56) References Cited

U.S. PATENT DOCUMENTS

| | | | |
|---|---|---|---|
| 4,914,022 A | * | 4/1990 | Furmanski et al. |
| 5,667,985 A | * | 9/1997 | O'Leary et al. |
| 6,207,408 B1 | * | 3/2001 | Essenfeld et al. |
| 6,291,180 B1 | * | 9/2001 | Chu |

* cited by examiner

Primary Examiner—Jan Ludlow
(74) Attorney, Agent, or Firm—Michael G. Petit

(57) ABSTRACT

A method for preserving cytological specimens for histological or histopathological use. A cytological sample from a biological tissue such as a tumor or a tumor cell line is dehydrated, disbursed and evenly distributed throughout a volume of molten material. The molten material is then drawn into a tubular member such as a pipette and allowed to solidify. Upon solidification, the cylindrical specimen is partially or completely extruded from the tube for further processing, including fixation, dehydration and molten paraffin infiltration and embedding as required for presentation to a sectioning device such as a microtome. Thin circular slices of the cylindrical specimen are removed from the cylindrical specimen and transferred to a slide, fixed and stained as desired. The device and method enable the production of a slide bearing a spatially homogeneous distribution of cytological material for microscopic examination.

3 Claims, 1 Drawing Sheet

PROCESS FOR PREPARING AND PRESENTING A TISSUE SAMPLE FOR HISTOLOGICAL STUDY

BACKGROUND OF THE INVENTION

1. Field of the Invention

The present invention relates to a method and apparatus for embedding and presenting tissue samples for histological examination and, more particularly, a method for preparing a tissue sample for microscopic examination.

2. Prior Art

A procedure for preparing tissue samples for microscopic examination by embedding the tissue in paraffin and slicing the paraffin-embedded tissue into thin layers with a microtome for mounting on a slide is well known in the art. Preparatory to embedding, the tissue is pretreated in various solutions selected in accordance with the particular examination being conducted. Typically, prior to paraffin embedding, the tissue sample is fixed, dehydrated, cleared, infiltrated with molten paraffin and, depending on the test, stained.

In order to impregnate the tissue sample, the sample is dehydrated, most commonly with isopropyl alcohol, and then immersed in liquid paraffin. The step of paraffin impregnation normally takes place at ambient pressure and at a temperature slightly higher than the melting point of the embedding material. In the event that the embedding material is paraffins, the melting point lies approximately between 50 degrees C. and 58 degrees C. The replacement of the isopropyl alcohol contained in the tissue of the tissue samples with paraffin is effected by dissolving the isopropyl alcohol in paraffin such that the concentration of the paraffin increases in the tissue sample. When the paraffin solidifies, thin sections can be sliced from the tissue samples embedded in paraffin block, mounted on a slide and examined under a microscope.

Berger, in U.S. Pat. No. 5,089,288, discloses a method of impregnating a tissue sample with paraffin in which a tissue sample, which has been fixed with isopropyl alcohol, is maintained under vacuum in a treatment vessel and the molten paraffin and tissue sample are simultaneously subjected to ultrasonic vibration effective to remove the isopropyl alcohol from the tissue sample and to impregnate the tissue sample with the paraffin.

McCormick, in U.S. Pat. No. 5,665,398, discloses a system for providing an embedded tissue specimen subsequent to fluid treatment of the specimen and preparatory to histological examination. The system includes the combination of a cassette for use in the preparation of tissue specimens for histological examination and an embedding mold having a first cavity for receiving the treated specimen and a second cavity for receiving the cassette. The system includes means for dispensing a predetermined amount of molten wax into the embedding mold.

U.S. Pat. No. 5,080,869 to McCormick describes a cassette for efficiently processing tissue samples. The cassette is stackable and can be used for preparing a plurality of specimens. The cassette generally includes a plurality of apertures disposed in the walls of the cassette for passage of processing fluids in a direction both orthogonal and parallel to the plane of the bottom wall of the cassette. The cassette also includes a sloping extension of the front wall of the cassette for ease in placing indicia on the cassette for identification of the sample. Further examples of systems and methods useful for preparing paraffin-impregnated tissue samples for histological examination are disclosed in U.S. Pat. Nos. 5,843,700 to Kerrod, et al., and 4,569,647 to McCormick.

A problem with the prior art methods of embedding and sectioning tissue is the clumping of cells such that cells of interest may not be present in a particular field of view. It is, therefore, desirable to have a method for preparing tissue for sectioning such that cells comprising the tissue are more or less evenly distributed on the section mounted on a slide thereby improving the probability of a particular cell type of interest being present in a particular section and field of view.

SUMMARY

It is a first object of the invention to provide a method for processing a tissue sample for mounting on a slide.

It is a further object of the invention to provide a method for preparing a tissue for sectioning wherein the cells comprising the tissue are substantially evenly distributed throughout the tissue preparation and a tissue section derived therefrom.

It is yet a further object of the invention to provide an apparatus and method for using the apparatus operable for preparing and presenting a tissue for sectioning.

It is an overall object of the invention to provide a method and apparatus for preparing a tissue sample for examination wherein the probability of a cell of interest being disposed within a field of view of the examiner is enhanced when compared with prior art methods of tissue sample preparation.

The features of the invention believed to be novel are set forth with particularity in the appended claims. However the invention itself, both as to organization and method of operation, together with further objects and advantages thereof may be best be understood by reference to the following description taken in conjunction with the accompanying drawings in which:

DESCRIPTION OF THE PREFERRED EMBODIMENTS

Figure 1:
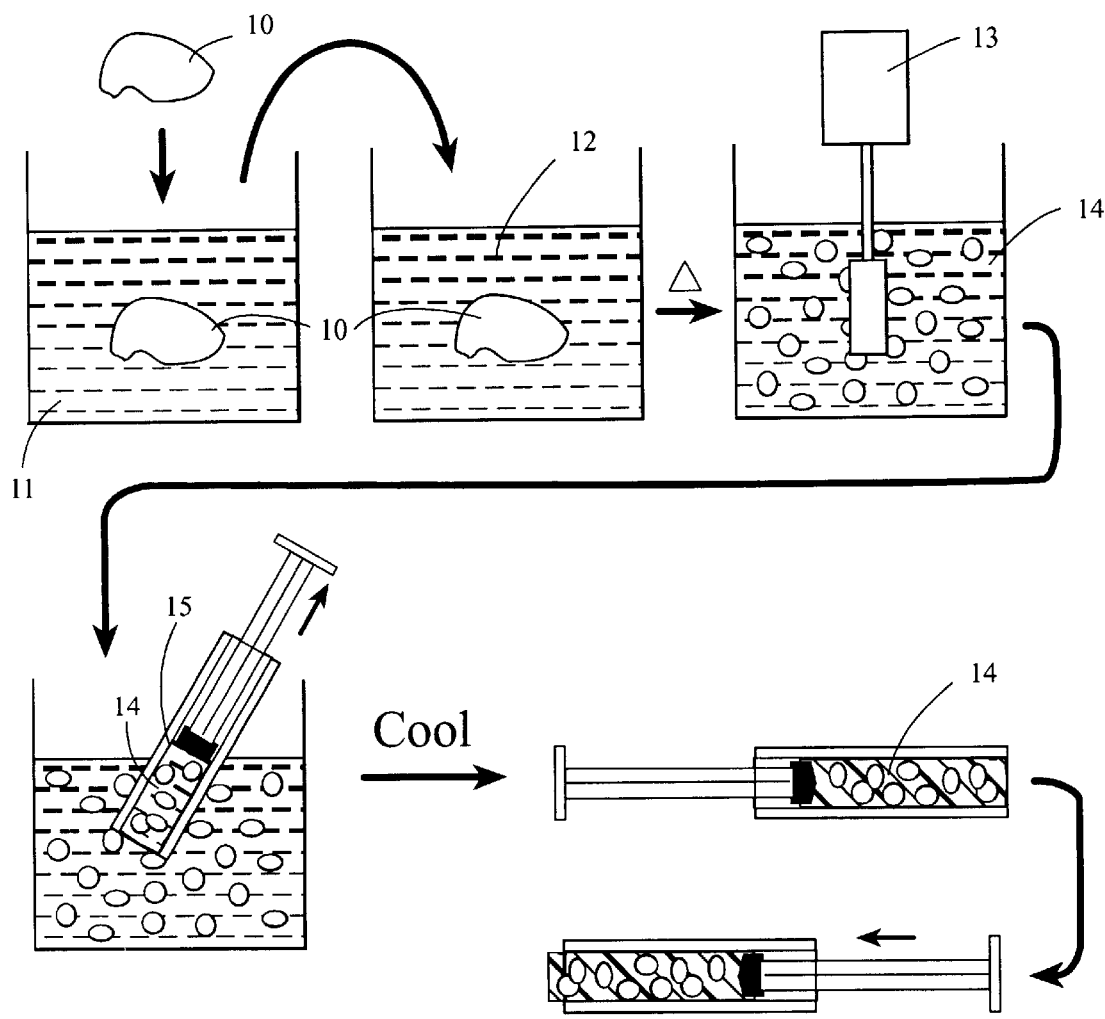
FIG. 1 is a schematic diagram illustrating the sequence of steps used for tissue sample preparation in accordance with the present invention.

The method for preparing a tissue sampling for storage and sectioning is illustrated diagrammatically in FIG. 1. A tissue sample 10 is prepared for embedding in a solid or semisolid support such as, for example, agarose or paraffins, by immersing the tissue in a suitable fluid medium, or a series of fluid mediums 11, to dehydrate and/or clear the tissue. The dehydrated tissue is then transferred into a volume of molten paraffins 12 and the tissue, which may comprise a cell line, fragmented and disbursed throughout the volume of melt by cell dispersing means 13 such as a sonicator or mechanical agitator.

After the cells comprising the tissue are disbursed throughout the volume of melt 14, a pipette 15 having an axial bore is employed to draw the volume of melt into the bore. The volume of melt containing the disbursed tissue is allowed to cool below its melting point within the axial bore. Upon hardening, the cylindrical plug thus formed within the axial bore may be totally or partially extruded from the pipette for storage and/or sectioning. The pipette may also be used to store the tissue. The extruded material may also be further processed as required for other examinations of the tissue such as electron microscopy or fluorescence spectrometry.

Figure 2:
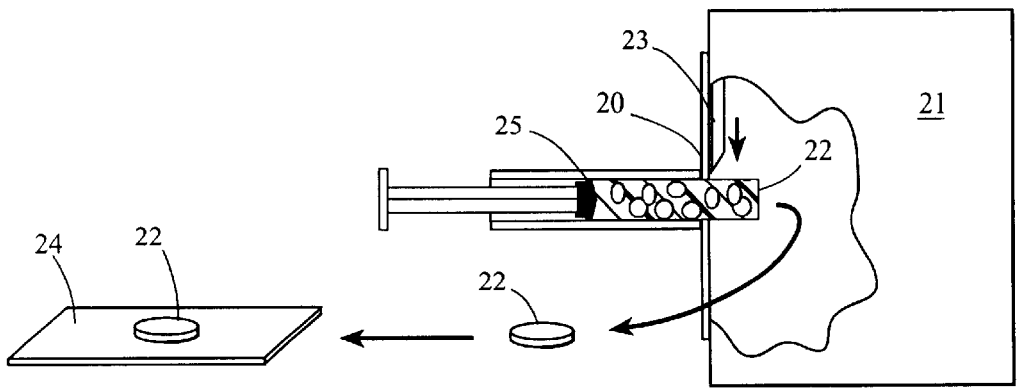
FIG. 2 is a longitudinal cross-sectional view of a preferred embodiment of a pipette operable for forming a cylindrical tissue specimen suitable for sectioning.

The pipette may be placed in a receiver port 20 in a microtome 21 and a thin disc 22 of the plug 14 extruded from the bore as shown in FIG. 2. A microtome blade 23 is advanced to separate the extruded disc from the plug. The disc 22 is then transferred to a support such as a microscope slide 24 for staining and examination. The diameter of the axial bore, and hence, the diameter of the plug and disc, may be "pin-like", having a diameter of ~0.1 mm. or "wafer-like", with a diameter of ~1.5 cm. or even greater. The pipette may be any, preferably rigid, tubular member. Preferred materials are glass and rigid or semi rigid elastomers such as polyethylene, polypropylene or polystyrene. The means for drawing the melt into the axial bore of the tube include vacuum aspiration, centrifugation and capillary action. A preferred means of vacuum aspiration is a plunger slidably disposed within the axial bore of the tubular member. While traditional paraffins may be used in accordance with the present method, a preferred embedding medium is a hydrophilic gel such as agarose.

In a variation of the method for preparing a portion of a tissue comprising cells for microscopic examination presented above, the tubular member comprises a polymeric material that remains a rigid at the melt temperature of the embedding medium and is easily separable from itself as, for example, by being sliced by a knife blade. The cylindrical plug of embedded tissue within the axial bore of the polymeric tubular member need not be extruded from the bore prior to mounting. In accordance with the alternate method, a portion of tissue is placed into a volume of a fluid embedding medium, then the cells comprising the tissue are disrupted until the cells comprising the portion are distributed substantially homogeneously throughout the volume of molten fluid embedding medium. A portion of the volume of the fluid embedding medium is drawn into the axial bore of the polymeric tubular member and permitted to solidify within the axial bore to form a cylindrical plug. After the cylindrical plug is formed, a portion of the tubular member (containing a portion of the cylindrical plug) is then transversely sliced or otherwise separated from the remainder of the tubular member to form a separated portion. The separated portion, which includes a thin disc of embedded cells circumferentially bounded by and contained within a ring comprising a portion of the polymeric tubular member, is then mounted on a rigid support substrate.

In accordance with the process of the present invention, the size of the sections can be controlled and the cells comprising the tissue are substantially homogeneously distributed within the plug and, therefore, a section removed therefrom. While particular embodiments of the present invention have been illustrated and described, it would be obvious to those skilled in the art that various other changes and modifications can be made without departing from the spirit and scope of the invention. For example, any fluid embedding material that can be solidified after being transferred to the axial bore of the tube such as upon standing, addition of a catalyst to the fluid or UV irradiation may be used in accordance with the present method. It is therefore intended to cover in the appended claims all such changes and modifications that are within the scope of this invention.

I claim:

1. A method for preparing a portion of a tissue comprising cells for microscopic examination comprising the steps of:
   (a) placing the portion of tissue into a volume of a fluid embedding medium, then
   (b) disrupting said portion until said cells comprising said portion are distributed substantially homogeneously throughout said volume of said fluid embedding medium; then
   (c) introducing a portion of said volume of said fluid embedding medium into an axial bore in a tubular member; then
   (d) solidifying said fluid embedding material within said axial bore to form a cylindrical plug; then
   (e) extruding a portion of said cylindrical plug from said axial bore and separating a portion of said cylindrical plug to form a separated portion; then
   (f) mounting said separated portion of said cylindrical plug on a rigid support substrate.

2. The method of claim 1 wherein said tissue is a cell line.

3. A method for preparing a portion of a tissue comprising cells for microscopic examination comprising the steps of:
   (a) placing the portion of tissue into a volume of a fluid embedding medium, then
   (b) disrupting said portion until said cells comprising said portion are distributed substantially homogeneously throughout said volume of said fluid embedding medium; then
   (c) introducing a portion of said volume of said fluid embedding medium into an axial bore in a tubular member; then
   (d) solidifying said fluid embedding material within said axial bore to form a cylindrical plug; then
   (e) separating a portion of said tubular member containing a portion of said cylindrical plug from said tubular member to form a separated portion; then
   (f) mounting said separated portion of said tubular member and cylindrical plug on a rigid support substrate.

* * * * *